(12) United States Patent
Silva

(10) Patent No.: US 10,941,383 B2
(45) Date of Patent: Mar. 9, 2021

(54) HUMAN BROWN ADIPOSE DERIVED STEM CELLS AND USES

(71) Applicant: BioRestorative Therapies, Inc., Melville, NY (US)

(72) Inventor: Francisco Javier Silva, Melville, NY (US)

(73) Assignee: BIORESTORATIVE THERAPIES, INC., Melville, NY (US)

(*) Notice: Subject to any disclaimer, the term of this patent is extended or adjusted under 35 U.S.C. 154(b) by 59 days.

(21) Appl. No.: 16/183,370

(22) Filed: Nov. 7, 2018

(65) Prior Publication Data
US 2019/0136194 A1 May 9, 2019

Related U.S. Application Data

(63) Continuation of application No. 14/255,595, filed on Apr. 17, 2014, now Pat. No. 10,167,449.

(60) Provisional application No. 61/906,087, filed on Nov. 19, 2013, provisional application No. 61/813,771, filed on Apr. 19, 2013.

(51) Int. Cl.
| C12N 5/0775 | (2010.01) |
| C12N 5/077 | (2010.01) |
| A61K 35/28 | (2015.01) |
| C12N 15/85 | (2006.01) |
| G01N 33/50 | (2006.01) |

(52) U.S. Cl.
CPC ............ *C12N 5/0667* (2013.01); *A61K 35/28* (2013.01); *C12N 5/0653* (2013.01); *C12N 15/85* (2013.01); *G01N 33/5073* (2013.01); *C12N 2510/04* (2013.01); *G01N 2500/10* (2013.01)

(58) Field of Classification Search
CPC .... C12N 5/0667; C12N 15/85; C12N 5/0653; C12N 2510/04; A61K 35/28; A61P 3/10
See application file for complete search history.

(56) References Cited

U.S. PATENT DOCUMENTS

| 5,198,357 | A | 3/1993 | Holmovist et al. |
| 5,226,914 | A | 7/1993 | Caplan et al. |
| 5,486,359 | A | 1/1996 | Caplan et al. |
| 5,736,396 | A | 4/1998 | Bruder et al. |
| 6,071,747 | A | 6/2000 | Strosberg et al. |
| 6,153,432 | A | 11/2000 | Halvorsen et al. |
| 7,273,756 | B2 | 9/2007 | Adkisson et al. |
| 7,824,711 | B2 | 11/2010 | Kizer et al. |
| 8,017,394 | B2 | 9/2011 | Adkisson, IV et al. |
| 8,192,759 | B2 | 6/2012 | Seyedin et al. |
| 10,167,449 | B2 * | 1/2019 | Silva .................. C12N 5/0667 |
| 2003/0224411 | A1 | 12/2003 | Stanton et al. |
| 2005/0124038 | A1 | 6/2005 | Aguiar et al. |
| 2005/0196387 | A1 | 9/2005 | Seyedin et al. |
| 2006/0073124 | A1 | 4/2006 | Garcia Castro et al. |
| 2006/0228391 | A1 | 10/2006 | Seyedin et al. |
| 2006/0251631 | A1 | 11/2006 | Adkisson, IV et al. |
| 2007/0128155 | A1 | 6/2007 | Seyedin et al. |
| 2008/0248003 | A1 | 10/2008 | Katz et al. |
| 2008/0299214 | A1 | 12/2008 | Seyedin et al. |
| 2009/0010896 | A1 | 1/2009 | Centeno et al. |
| 2009/0012629 | A1 | 1/2009 | Yao et al. |
| 2009/0143867 | A1 | 6/2009 | Gage et al. |
| 2009/0214491 | A1 | 8/2009 | Burt |
| 2009/0274665 | A1 | 11/2009 | Akabuto et al. |
| 2009/0304643 | A1 | 12/2009 | Khurgel et al. |
| 2010/0150885 | A1 | 6/2010 | Tseng et al. |
| 2010/0168022 | A1 | 7/2010 | Centeno |
| 2010/0322994 | A1 | 12/2010 | Kizer et al. |
| 2011/0117066 | A1 | 5/2011 | Ailhaud et al. |
| 2011/0256095 | A1 | 10/2011 | Seyedin et al. |
| 2012/0009224 | A1 | 1/2012 | Kizer et al. |
| 2012/0009270 | A1 | 1/2012 | Kizer et al. |
| 2012/0087948 | A1 | 4/2012 | Kizer et al. |
| 2012/0107384 | A1 | 5/2012 | Yao et al. |
| 2013/0074199 | A1 | 3/2013 | Spiegelman et al. |
| 2013/0084341 | A1 | 4/2013 | Centeno |
| 2013/0209418 | A1 * | 8/2013 | Seyda .................. A61K 35/35 424/93.7 |
| 2014/0017789 | A1 | 1/2014 | Silva et al. |

(Continued)

FOREIGN PATENT DOCUMENTS

| JP | 2010-130968 A | 6/2010 |
| WO | WO 2008/034803 A1 | 3/2008 |

(Continued)

OTHER PUBLICATIONS

Ahfeldt, T. et al., "Programming human pluripotent stem cells into white and brown adipocytes", Nature Cell Biol., vol. 14, No. 2, 209-219, Feb. 2012.
Alhadlaq et al., "Mesenchymal Stem Cells: Isolation and Therapeutics," Stem Cells and Development, 13:436-448, 2004.
Bernardo et al., "Optimization of In Vitro Expansion of Human Multipotent Mesenchymal Stromal Cells for Cell-Therapy Approaches: Further Insights in the Search for a Fetal Calf Serum Substitute," Journal of Cellular Physiology, 211:121-130, 2007.
Blande et al., "Adipose tissue mesenchymal stem cell expansion in animal serum-free medium supplemented with autologous human platelet lysate", Transfusion 49: 2680-5, 2009.
Bukowiecki et al., "Proliferation and differentiation of brown adipocytes from interstitial cells during cold acclimation", American Journal of Physiology 250, C880-C887, 1986.

(Continued)

*Primary Examiner* — Blaine Lankford
(74) *Attorney, Agent, or Firm* — K&L Gates LLP

(57) ABSTRACT

An isolated human brown adipose tissue stem cell line. In one embodiment, the isolated human brown adipose tissue stem cell line expresses the markers CD9, SSEA4, CD44, CD90, CD166, CD73, but not CD14, CD34, CD45 or STRO-1. In another embodiment, the isolated human brown adipose tissue stem cell line expresses the genes UCP1, PPARGC1A, NRF1, FOXC2, CREB1, SIRT3, and WNT5A (REFX). In still another embodiment, the isolated human brown adipose tissue stem cell line is capable of differentiating into osteoblasts, chondrocytes, and adipocytes.

13 Claims, 23 Drawing Sheets
(18 of 23 Drawing Sheet(s) Filed in Color)

(56) References Cited

U.S. PATENT DOCUMENTS

| | | |
|---|---|---|
| 2014/0023622 A1 | 1/2014 | Silva et al. |
| 2014/0038177 A1 | 2/2014 | Silva et al. |
| 2014/0212875 A1 | 7/2014 | Silva et al. |
| 2015/0166958 A1 | 6/2015 | Kishida et al. |

FOREIGN PATENT DOCUMENTS

| | | |
|---|---|---|
| WO | WO 2009/006161 A1 | 1/2009 |
| WO | WO 2009/137613 A2 | 11/2009 |
| WO | WO 2009/156413 A1 | 12/2009 |

OTHER PUBLICATIONS

Cannon et al., "Cultures of Adipose Precursor Celis from Brown Adipose Tissue and of Clonal Brown-Adipocyte-Like Cell Lines," Methods in Molecular Biology, 155:213-224, 2001.
Cannon et al., "Brown Adipose Tissue: Function and Physiological Significance", Physiol. Rev. 84:277-359, 2004.
Caplan, "Mesenchymal Stem Cells," Journal of Orthopaedic Research, 9:641-650, 1991.
Caplan et al., "Mesenchymal stem cells: building blocks for molecular medicine in the 21st century," Trends in Molecular Medicine, 7(6):259-264, Jun. 2001.
Casteilla et al., "Differentiation of ovine brown adipocyte precursor cells in a chemically defined serum-free medium," European Journal of Biochemistry, 198(1):195-99, 1991.
Crisostomo et al., "High Passage Number of Stem Cells Adversely Affects Stem Cell Activation and Myocardial Protection," SHOCK, 26(6):575-580, 2006.
Cypress et al., "Identification and Importance of Brown Adipose Tissue in Adult Humans", New England Journal of Medicine, 360:1509-1517, 2009.
Folgiero et al., "Purification and Characterization of Adipose-Derived Stem Cells from Patients with Lipoaspirate Transplant", Cell Transplantation, vol. 19, 2010, 1225-1235.
Freshney, Culture of Animal Cells, A Manual of Basic Technique, Third edition, Wiley-Liss, New York, 1994.
Deschaseaux et al., "Direct selection of human bone marrow mesenchymal stem cells using an anti-CD49a antibody reveals their CD45med.low phenotype," British Journal of Haematology, 122:506-517, 2003.
Doucet et al., "Platelet Lysates Promote Mesenchymal Stem Cell Expansion: A Safety Substitute for Animal Serum in Cell-Based Therapy Applications," Journal of Cellular Pysiology, 205:228-236, 2005.
EMBL sequence data bank accession No. X56545.1, NCBI BLAST search performed Jun. 9, 2014 from NCBI website.
Fortier et al., "Isolation and chondrocytic differentiation of equine bone marrow-derived mesenchymal stem cells," AJVR, 59(9):1182-1187, Sep. 1998.
Hauner et al., "Promoting effect of glucocorticoids on the differentiation of human adipocyte precursor cells cultured in a chemically defined medium", J. Clin. Invest., vol. 84, Nov. 1989, pp. 1663-1670.
Huss, "Perspectives on the Morphology and Biology of CD34-Negative Stem Cells," Journal of Hematotherapy & Stem Cell Research, 9:783-793, 2000.
Kajimura et al., "Initiation of myoblast to brown fat switch by a PRDM16—C/EBP-β transcriptional complex", Nature, vol. 460, 1154-1158, Aug. 2009.
Kajimura et al., "Transcriptional control of brown fat development", Cell Metabolism, 11(4): 257-262, Apr. 2010.
Kang et al., "Role of c-Jun N-terminal Kinase in the PDGF-Induced Proliferation and Migration of Human Adipose Tissue-Derived Mesenchymal Stem Cells," Journal of Cellular Biochemistry, 95:1135-1145, 2005.
Kim et al., "Role of CD9 in proliferation and proangiogenic action of human adipose-derived mesenchymal stem cells," Pflügers Archiv—European Journal of Physiology, 455:288-296, 2007.

Klein et al., "β3-Adrenergic Stimulation Differentially Inhibits Insulin Signaling and Decreases Insulin-induced Glucose Uptake in Brown Adipocytes", The Journal of Biological Chemistry, vol. 274, No. 49, Dec. 3, 1999, 34795-34802.
Lange et al., "Accelerated and Safe Expansion of Human Mesenchymal Stromal Cells in Animal Serum-Free Medium for Transplantation and Regenerative Medicine," J. Cell. Physiol. 213:18-26, 2007.
Lean, M. E. J., "Brown Adipose Tissue in Man," Proceedings of the Nutrition Society, 1989, 48: 243-256.
Lee et al., "Inducible Brown Adidpogenesis of Supraclaicular Fat in Adult Humans," Endocrinology, 152(10):359703602, Oct. 2011.
Müller et al., "Animal serum-free culture conditions for isolation and expansion of multipotent mesenchymal stromal cells from human BM," Cytotherapy 8(5):437-444, 2006.
Nedergaard et al., "Unexpected evidence for active brown adipose tissue in adult humans", Am J Physiol Endocrinol Metab 293: E444-E452, 2007, May 1, 2007.
Niemeyer et al., "Comparison of Immunological properties of Bone Marrow Stromal Cells and Adipose Tissue-Derived Stem Cells Before and After Osteogenic Differentiation In Vitro," Tissue Engineering, 13(1):111-121, 2007.
Riordan et al., "Non-expanded adipose stromal vascular fraction cell therapy for multiple sclerosis", Journal of Translational Medicine, 7(29): 1-9, 2009.
Rousseau et al., "Brown fat in breast cancer patients: analysis of serial (18)F-FDG PET/CT scans", European Journal of Nuclear Medicine and Molecular Imaging, Jul. 2006, vol. 33, No. 7: 785-791.
Sato et al., "Reversible Expression of CD34 by Murine Hematopoietic Stem Cells," Blood, 94:2548-2554, 1999.
Schallmoser et al., "Human platelet lysate can replace fetal bovine serum for clinical-scale expansion of functional mesenchymal stromal cells," Transfusion, 47:1436-1446, 2007.
Seale et al., "Transcriptional control of brown fat determination by PRDM16", Cell Metabolism 6: 38-54, 2007.
Tapp et al., "Adiose-Derived System Cells: Characterization and Current Application in Orthopaedic Tissue Repair," Experimental Biology and Medicine 234:1-9, 2009.
Tondreau et al., "Isolation of BM mesenchymal stem cells by plastic adhesion or negative selection: phenotype, proliferation kinetics and differentiation potential," Cytotherapy, 6(4):372-379, 2004.
Tran et al., "Transplantation of adipose tissue and stem cells: role in metabolism and disease," Nature Reviews/Endocrinology, 6(4):195-213, Apr. 2010.
International Search Report and the Written Opinion of the International Searching Authority for PCT/US2012/044651, dated Nov. 9, 2012, 35 pages.
H. Ning, et al. "Mesenchymal Stem Cell Marker Stro-1 is a 75kd Endothelial Antigen," Biochem Biophys Res Comm., Author Manuscript; available in PMC Sep. 23, 2012; Published in final form Sep. 23, 2011; 413(2): 353-357.
Silva. et al.. "Metabolically Active Human Brown Adipose Tissue Derived Stem Cells," Stem Cells, vol. 32, No. 2, pp. 572-581, Feb. 13, 2014.
Patel, et al., "Putative Population of Adipose-Derived Stem Cells Isolated From Mediastinal Tissue During Cardiac Surgery," Cell Transplantation, vol. 22, pp. 507-511, 2013.
Hernandez, et al., "Dexamethasone Inhibits Growth Factor-Induced Type 3 Deiodinase Activity and mRNA Expression in a Cultured Cell Line Derived from Rat Neonatal Brown Fat Vascular-Stromal Cells," Endocrinology 143 D (7), pp. 2652-2658, Jul. 1, 2002.
Cigolini, et al., "Human Brown Adipose Cells in Culture," Experimental Cell Research, vol. 159, No. 1, pp. 261-266, Jul. 1, 1985.
Schulz, et al., "Identification of inducible brown adipocyte progenitors residing in skeletal muscle and white fat," Proceedings of the National Academy of Sciences, vol. 108, No. 1, pp. 143-148, Jan. 4, 2011.
Klein, et al., "Novel adipocyte lines from brown fat: a model system for the study of differentiation, energy metabolism, and insulin action," BioEssays vol. 24, pp. 382-388, Wiley Periodicals, Inc., Jan. 1, 2002.

(56) References Cited

OTHER PUBLICATIONS

PCT International Search Report and Written Opinion of International Searching Authority for International Patent Application No. PCT/US2014/034540, dated Jul. 22, 2014, 13 pages.

* cited by examiner

|  | CD90 | CD166 | STRO-1 | CD45 | CD133 | CD34 | SSEA-4 | CD44 | CD106 | CD80 |
|---|---|---|---|---|---|---|---|---|---|---|
| BADSC | 99.6 | 100 | 0 | 0 | 0 | 0 | 97.7 | 100 | 0 | 0 |
| WADSC | 98.9 | 98.9 | 1.3 | 1 | 0.7 | 2 | 8.8 | 100 | 1.6 | 2 |

|  | LIN | DR,DP,DQ | CD73 | CD117 | CD105A,B,C | CD86 | CD63 | CD9 |
|---|---|---|---|---|---|---|---|---|
| BADSC | 1.4 | 0 | 100 | 0 | 98.3 | 0 | 86 | 100 |
| WADSC | 11 | 0.5 | 99 | 1 | 68.3 | 2 | 99 | 95 |

Fig. 3(b)

HUMAN BROWN ADIPOSE DERIVED STEM CELLS AND USES

RELATED APPLICATIONS

The present application is a continuation application of co-pending U.S. patent application Ser. No. 14/255,595 filed on Apr. 17, 2014, which claims priority to and benefit of U.S. Provisional Application No. 61/906,087 filed Nov. 19, 2013 and U.S. Provisional Application No. 61/813,771 filed Apr. 19, 2013. Each of the forgoing applications is hereby incorporated by reference in its entirety into the present application.

FIELD

The invention relates generally to the field of cell culture and more specifically to the field of determining cell type.

BACKGROUND

Brown adipose tissue (BAT) plays a key role in the evolutionarily conserved mechanisms underlying energy homeostasis in mammals. It is characterized by fat vacuoles 5-10 microns in diameter and expression of uncoupling protein 1 (UCP1), central to the regulation of thermogenesis. In the human newborn, depots of BAT are typically grouped around the vasculature and solid organs. These depots maintain body temperature during cold exposure by warming the blood before its distribution to the periphery. They also ensure an optimal temperature for biochemical reactions within solid organs. BAT had been thought to involute throughout childhood and adolescence. Recent studies, however, have confirmed the presence of active brown adipose tissue in adult humans, with depots residing in cervical, supraclavicular, mediastinal, paravertebral and/or suprarenal regions, for example. Also, it has also been reported that BAT, alternatively called beige fat can be found within white adipose tissue (WAT).

SUMMARY

The present disclosure presents an implantable construct that can be used to treat metabolic disorders, such as but not limited to, diabetes and obesity.

Provided herein is an implantable construct comprising a scaffold and an isolated human neonatal brown adipose tissue stem cell cultured on the scaffold. The isolated human neonatal brown adipose tissue stem cell can be cultured in a culture medium comprising fibronectin type III domain-containing protein 5 (FNDC5) and differentiate into a human neonatal brown adipose tissue differentiated cell. UCP-1, ELOVL3, and PGC1A gene expression can be upregulated in the human neonatal brown adipose tissue differentiated cell.

Also provided herein is an implantable construct comprising a scaffold and a human neonatal brown adipose tissue differentiated cell derived from an isolated human neonatal brown adipose tissue stem cell. The isolated human neonatal brown adipose tissue stem cell can be grown in a culture medium comprising fibronectin type III domain-containing protein 5 (FNDC5) and differentiate into the human neonatal brown adipose tissue differentiated cell. UCP-1, ELOVL3, and PGC1A gene expression can be upregulated in the human neonatal brown adipose tissue differentiated cell.

Also provide herein is an implantable construct comprising a scaffold and an isolated human neonatal brown adipose tissue stem cell cultured on the scaffold. The isolated human neonatal brown adipose tissue stem cell can be cultured in a culture medium and differentiate into a human neonatal brown adipose tissue differentiated cell.

It is understood that the inventions described in this specification are not limited to the examples summarized in this Summary. Various other aspects are described and exemplified herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The present teachings described herein will be more fully understood from the following description of various illustrative embodiments, when read together with the accompanying drawings. It should be understood that the drawings described below are for illustration purposes only and are not intended to limit the scope of the present teachings in anyway.

FIGS. 3(a)-1, 3(a)-2, and 3(a)-3 are a series of flow cytometry and immunocytochemistry graphs for cell surface markers on neonatal brown adipose derived stem cells;

FIG. 3(b) is a table of comparisons of expression levels for various markers for neonatal brown adipose derived stem cells and white adipose derived stem cells;

DETAILED DESCRIPTION

A population of metabolically active brown adipose tissue stem cells has been isolated from a one day old male newborn. The stem cell population, termed "neonate brown adipose derived stem cells" (neonate BADSCs) demonstrated the potential to: (1) be expanded in vitro; (2) exhibit multi-lineage potential; and (3) functionally differentiate into metabolically active brown adipocytes. Such a stem cell population could offer new cell-based means to restore and enhance energy homeostasis in vivo for the treatment of obesity and related metabolic disorders. These stem cells also are a useful tool for studying adipose tissue biology.

Figure 1:
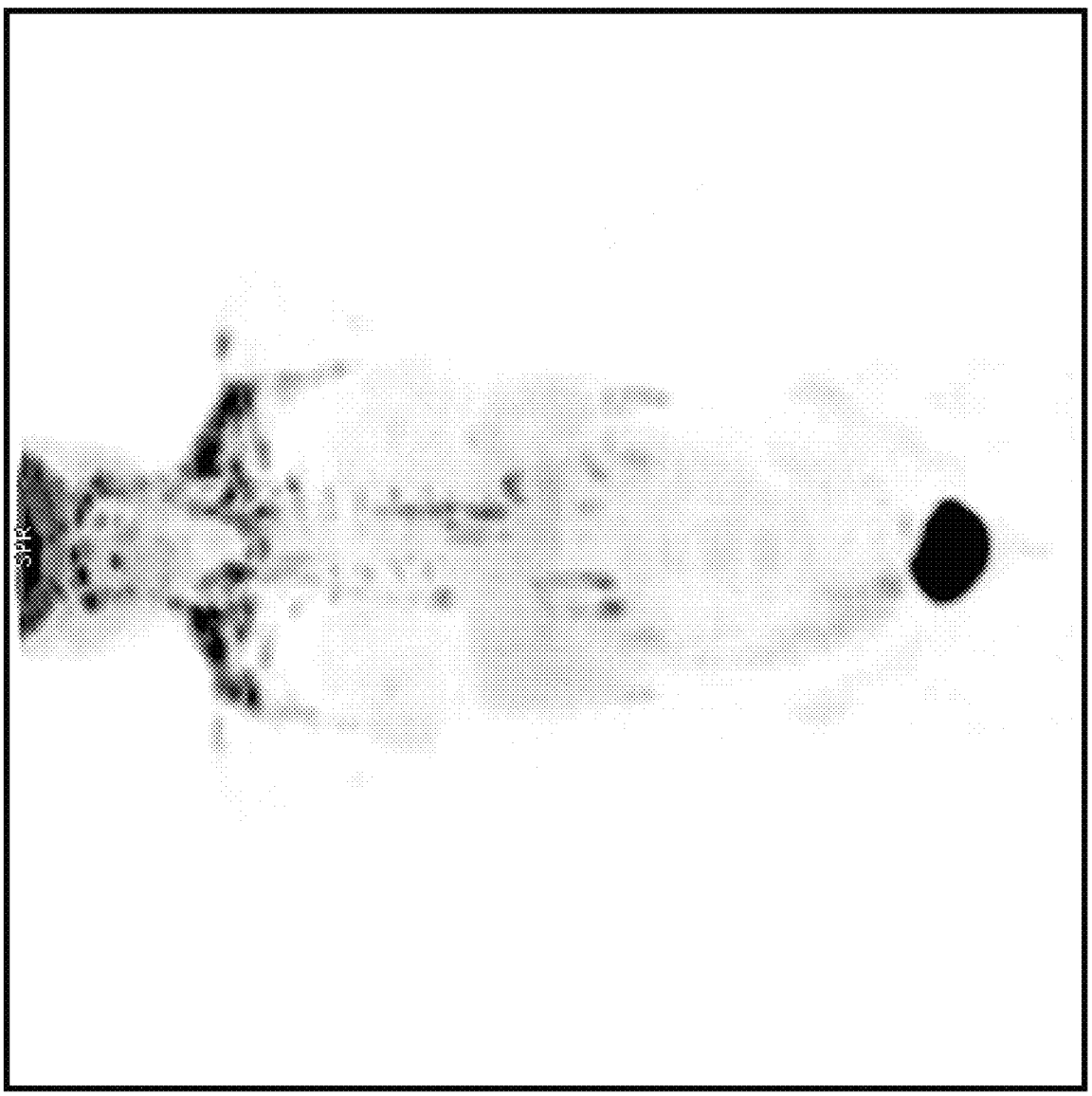
FIG. 1 is a PET scan of 18F-FDG uptake in an adult.
Figure 2B:
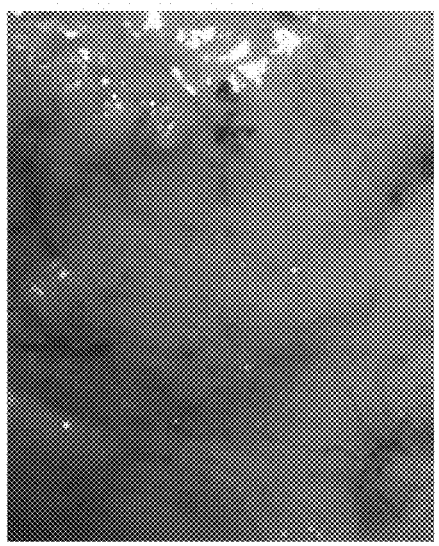
FIG. 2(b) is a photograph of mediastinal adipose tissue from a 56 year old.
Figure 2D:
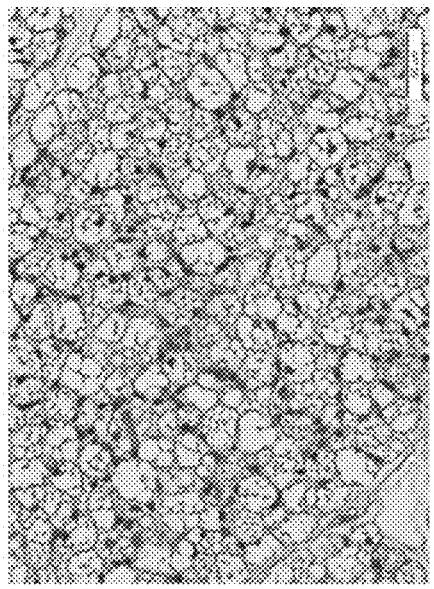
FIG. 2(d) is a photomicrograph of a section of the tissue of FIG. 2(a)
Figure 2A:
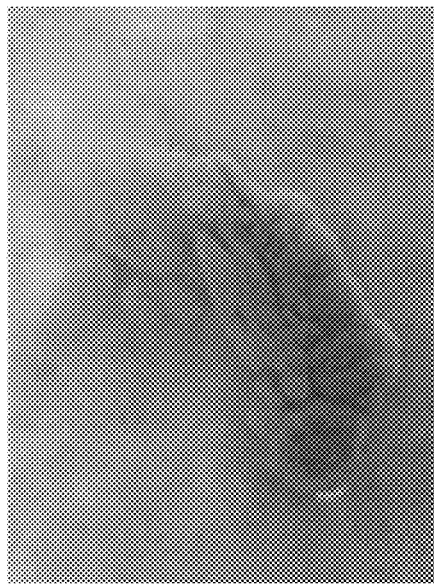
FIG. 2(a) is a photograph of mediastinal adipose tissue from a neonate.
Figure 2C:
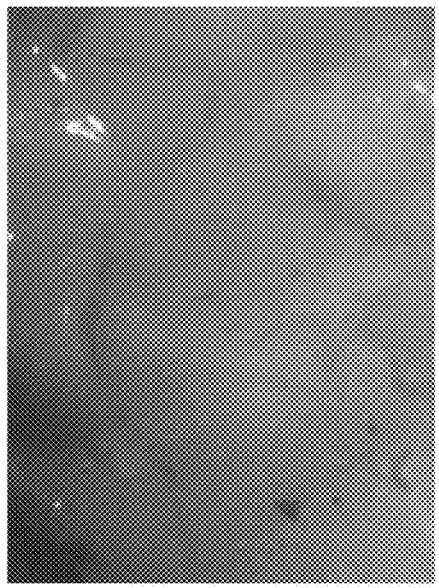
FIG. 2(c) is a photograph of mediastinal adipose tissue from an 80 year old.
Figure 2F:
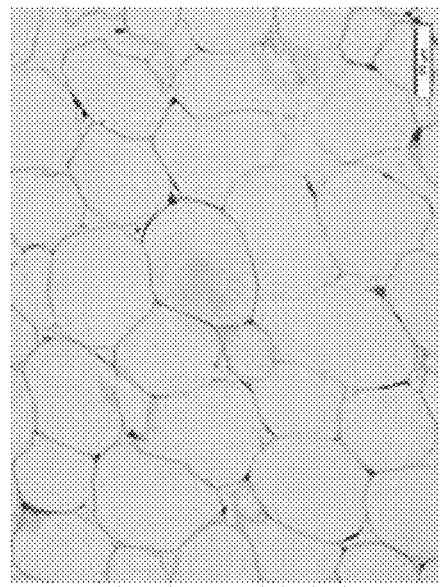
FIG. 2(f) is a photomicrograph of a section of the tissue of FIG. 2(c)
Figure 2E:
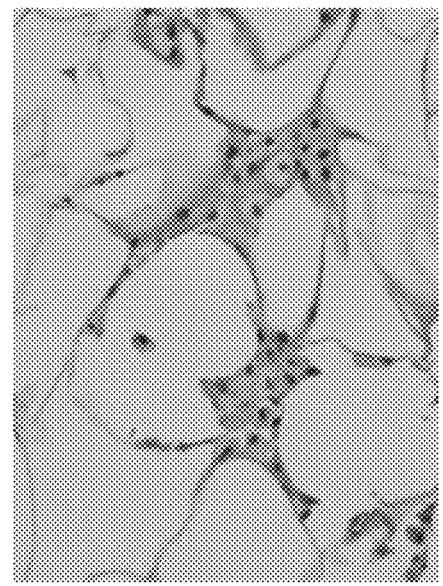
FIG. 2(e) is a photomicrograph of a section of the tissue of FIG. 2(b)
Figure 8:
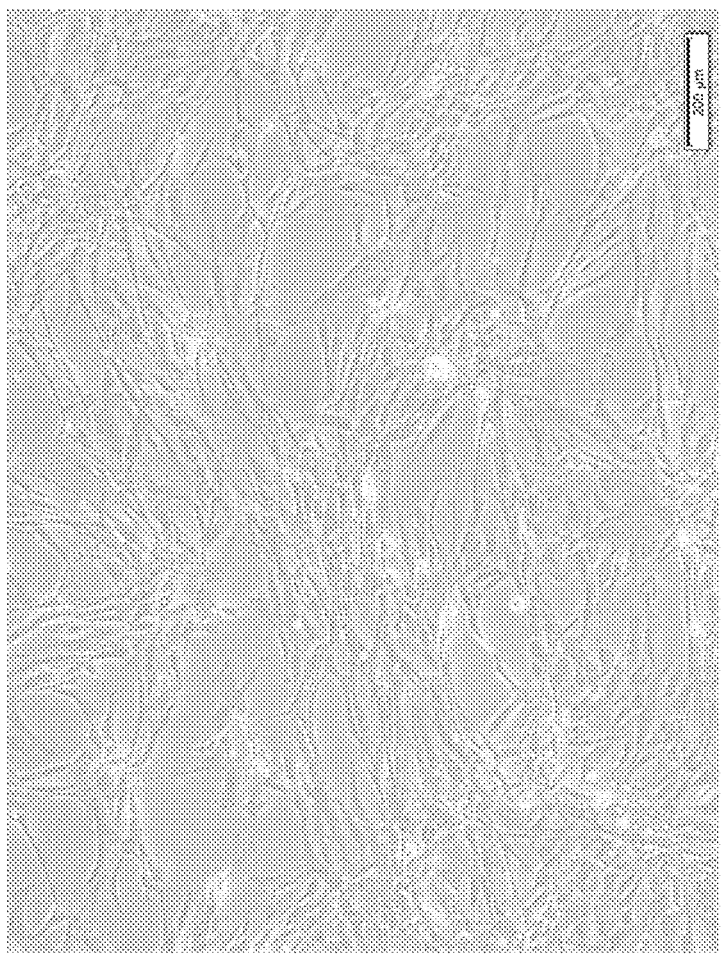
FIG. 8 is a photomicrograph of transfected BADSC showing normal cell morphology.

In order to identify a stem cell population within newborn mediastinal brown adipose depots, explants were generated and plated into tissue culture plates. Adherent cells were successfully derived from the brown adipose tissue explants, these primary cell cultures were fed every 3 days in media comprising DMEM low glucose, 1× Glutamax, 1× NEAA, and 10% platelet lysate. In order to define a clonal population of cells, cell lines were derived by single-cell plating in 96 well plates. Confluency was reached at 6 days and the cells exhibited Mesenchymal Stem Cell (MSC)-like morphology, as depicted in FIG. 8. Mediastinal brown adipose tissue from a 56 year old and an 80 year old are shown in FIGS. 2b and 2c, respectively, for comparison with the newborn mediastinal brown adipose tissue, as depicted in FIG. 2a. The decrease in the brown adipose tissue is evident. FIGS. 2d-2f are photomicrographs of H/E sections taken of the biopsied tissues of FIGS. 2a-2c, respectively.

Growth kinetics of the clonal cell population demonstrated that the population could be propagated for greater than 90 passages. Karyotyping of the clonal cell population at passage 7 demonstrated normal diploid cells without chromosomal aberrations.

Figures 1, 3A:
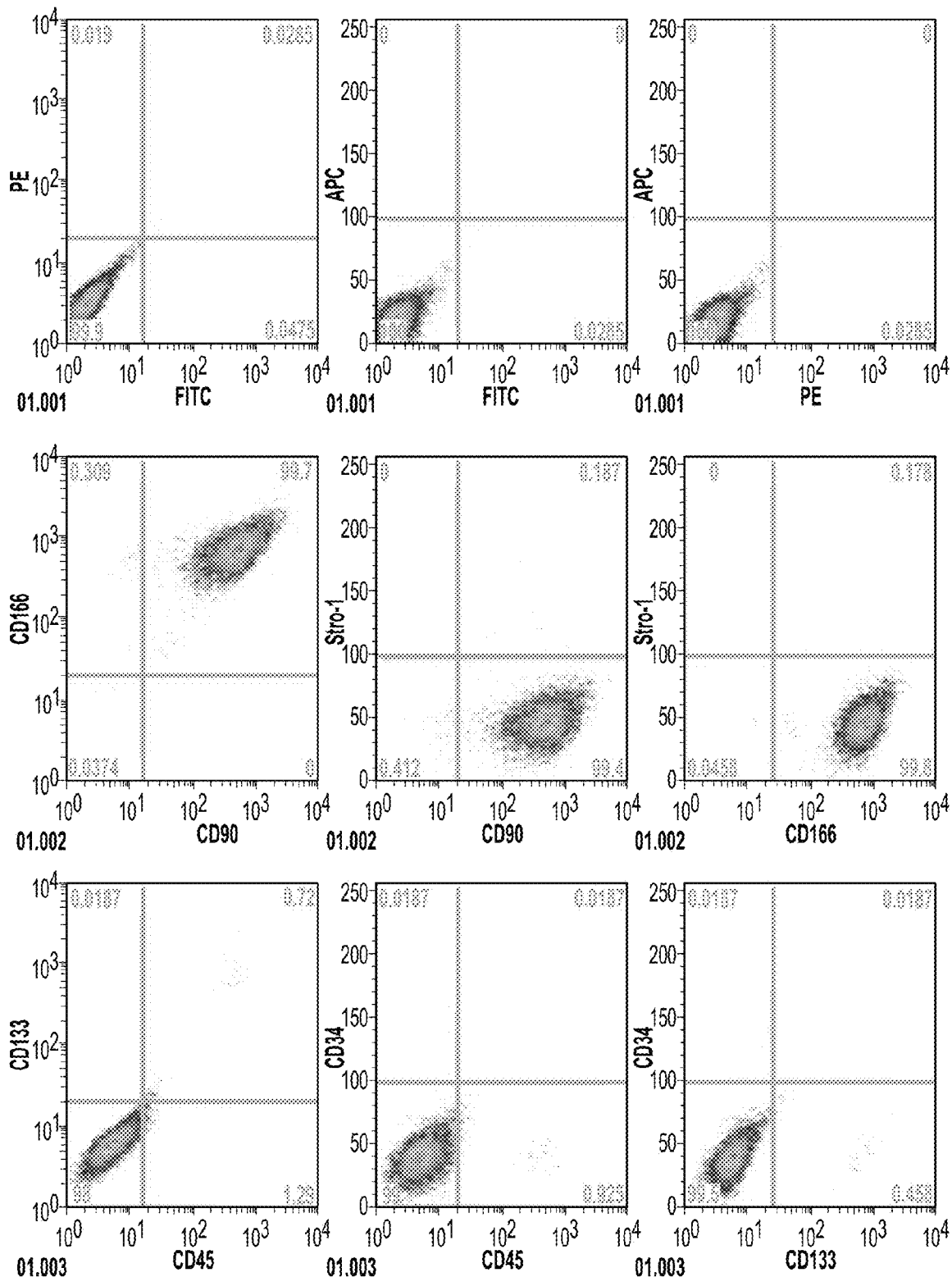
Figures 2, 3A:
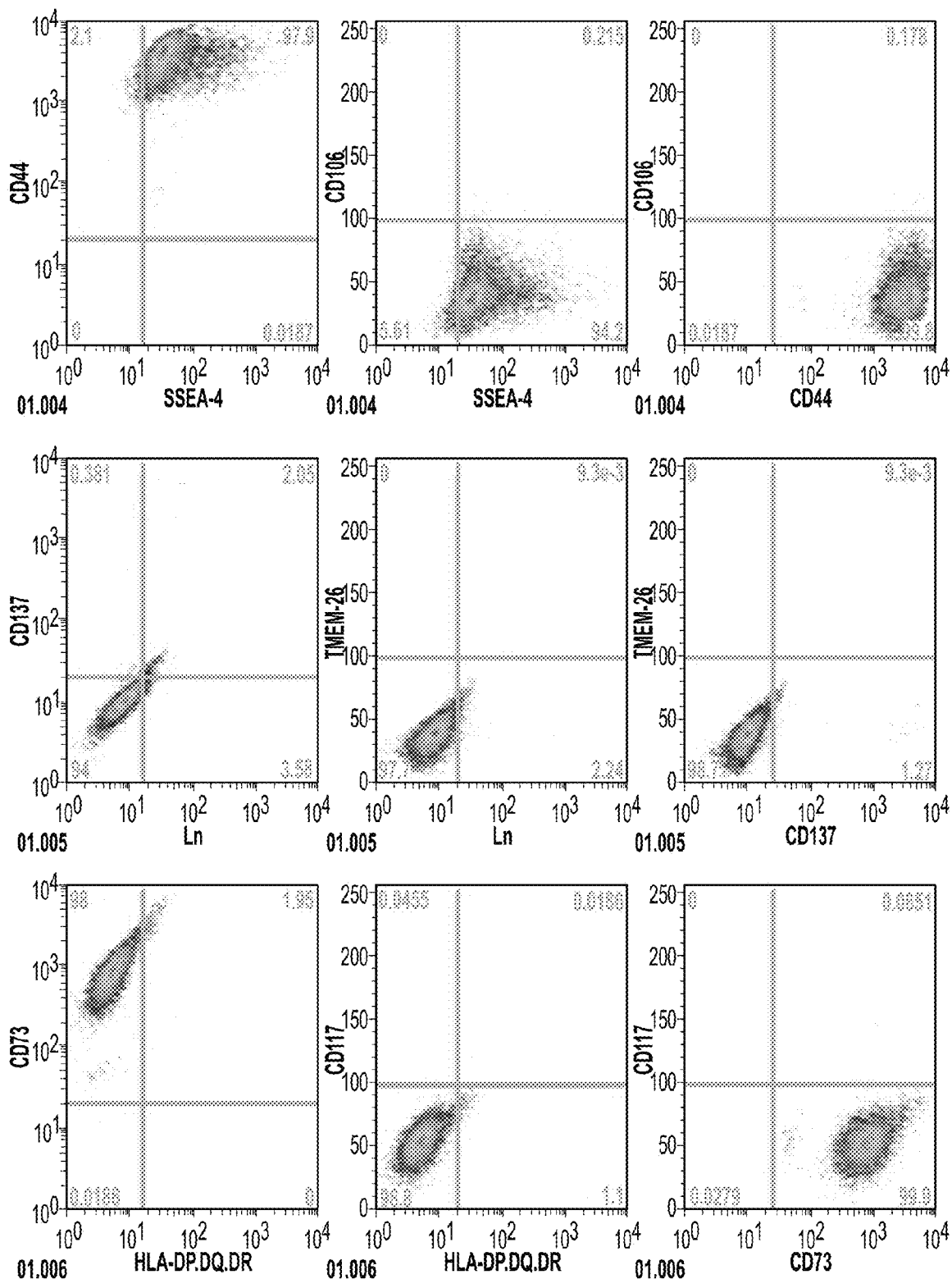
Figures 3, 3A:
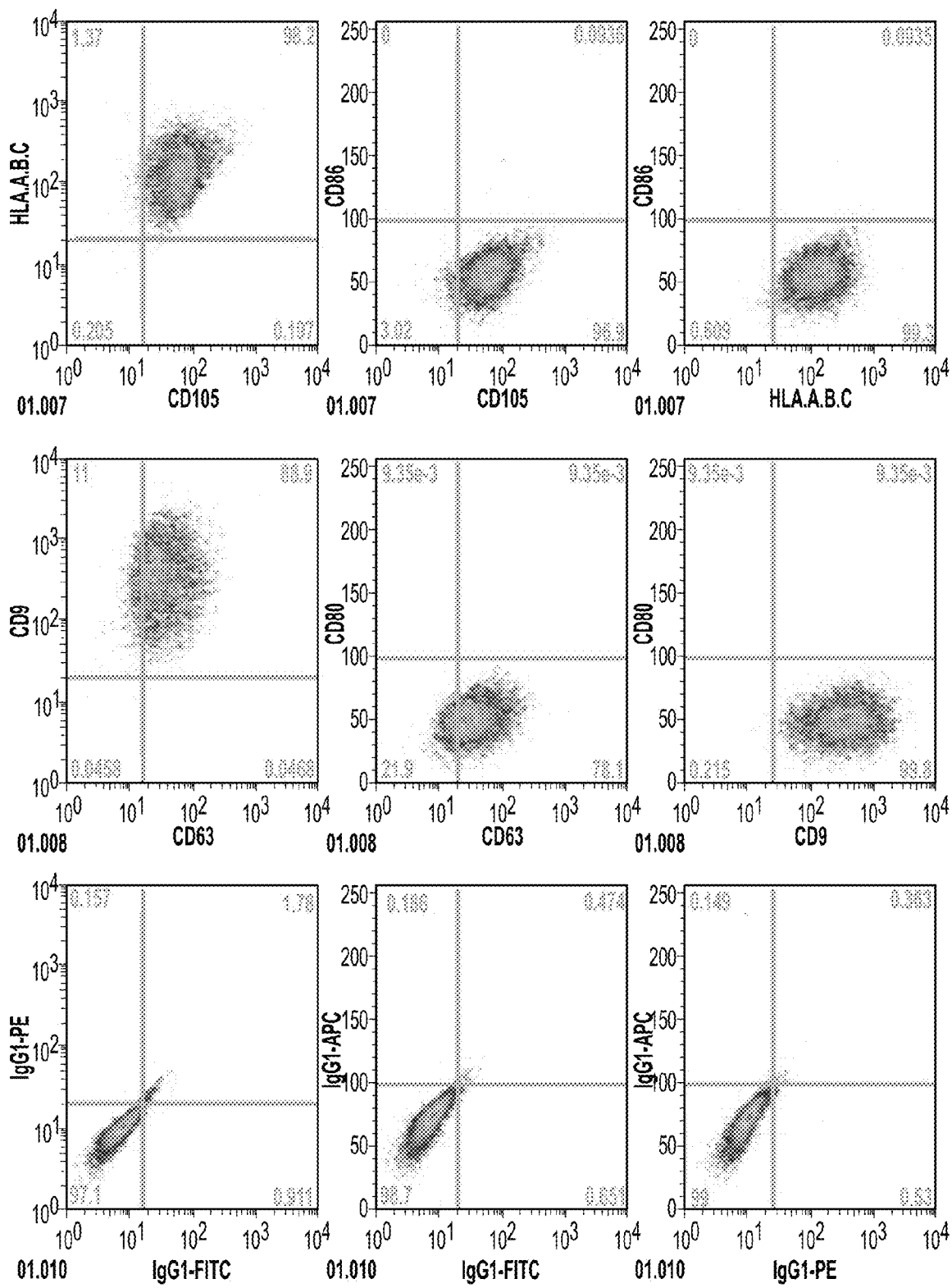

Referring to FIGS. 3(a) and (3b), to further characterize these neonate BADSC, flow cytometry, and immunocytochemistry were used. The neonate BADSC were found to exhibit characteristics that are similar to other MSCs but are not identical. For instance, the neonate BADSC were positive for CD9, SSEA4, CD44, CD90, CD166, and CD73, but were negative for hematopoietic markers CD14, CD34, and CD45. Furthermore, the neonate BADSC did not express STRO-1, which has been previously found to be expressed in mesenchymal stem cells derived from various tissues.

Figure 3C:
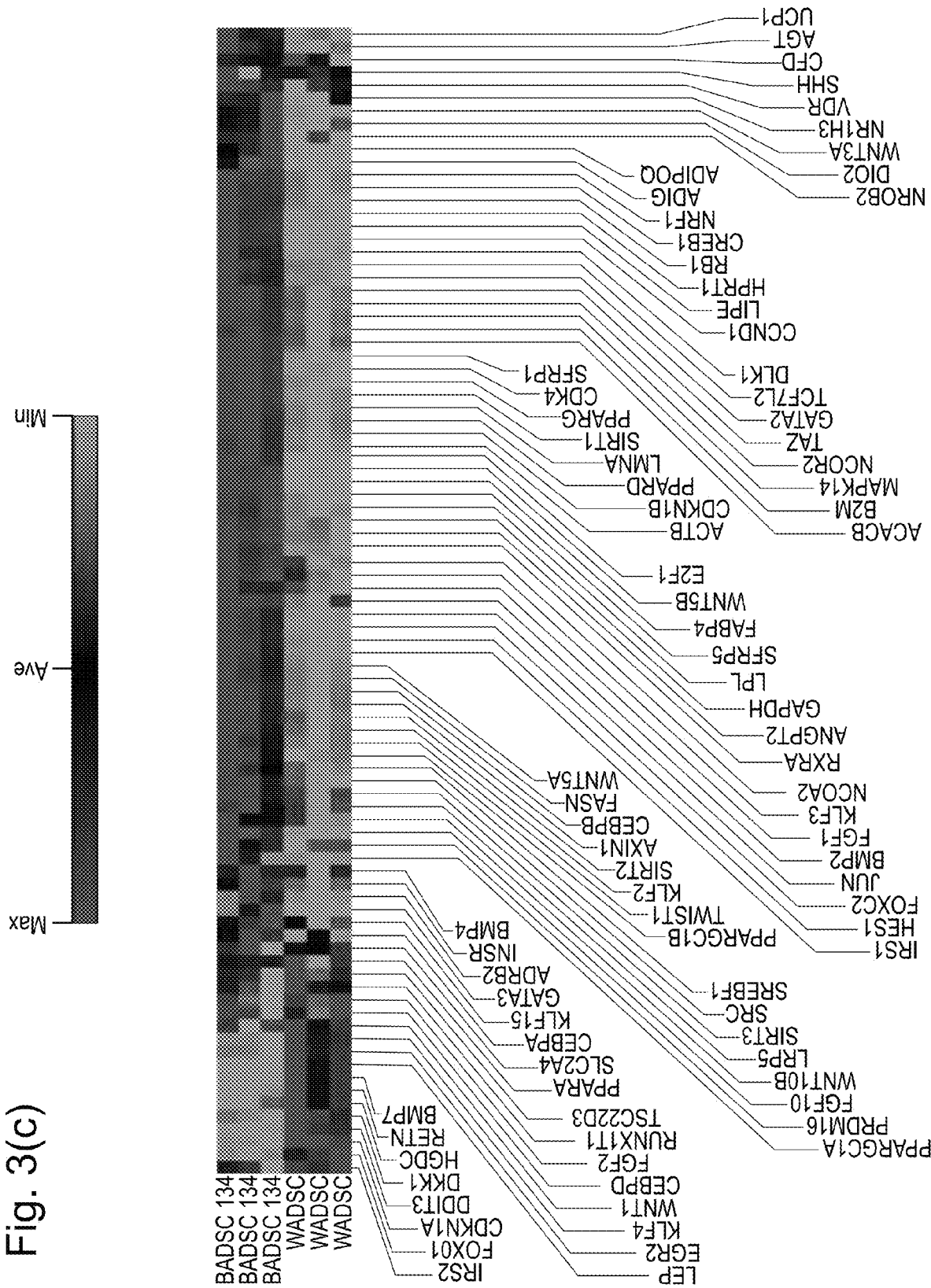
FIG. 3(c) is a gene expression profile for neonatal brown adipose derived stem cells (BADSC) and white adipose derived stem cells (WADSC)

An analysis of the gene expression profiles of passage 2 neonate BADSC demonstrate that the neonate BADSC have a distinct gene expression profile, as depicted in FIG. 3(c), in comparison with white adipose derived stem cells. The genes whose expression is enriched in BADSC include pro-brown adipose selective genes such as, for example, CREB1, DIO2, IRS1, MAPK14, NRF1, FOXC2, PPARD, PGC1-A, PGC1-B, PRDM16, SRC, UCP1, and WNT5A. The cells also express higher levels of anti-white adipose tissue genes, such as GATA2, KLF2, and KLF3. Importantly, expression of these pro-brown selective genes can distinguish brown adipose derived stem cells from stem cells derived from white adipose depots.

Passage 2 neonate BADSC were induced to differentiate into osteo, chondro, white, and brown adipogenic cell lineages to determine multi-lineage potential. After three weeks of induction the cells demonstrated the ability to differentiate into osteoblasts, chondrocytes, and adipocytes. When induced to differentiate under osteogenic promoting conditions, the cells formed a mineralized matrix, which was confirmed by alizarin red staining; immunocytochemistry staining of osteocalcin, and RT-PCR analysis for osteopontin, osteonectin, and alkaline-phosphatase, further confirmed differentiation. Chondrogenic differentiation was confirmed by alcian blue staining for sulfated proteoglycans on induced cell pellets. RT-PCR confirmed expression of collagen 2A, biglycan, and A6, which are markers of chondrogenic differentiation. White adipogenic differentiation was confirmed by Oil Red O staining of lipid droplets. Immunocytochemistry confirmed expression of FABP4, and RT PCR confirmed expression of FABP4, LPL, and PPARγ, which are markers of adipogenic differentiation.

Real-time qPCR of neonatal brown adipose-differentiated cells demonstrated upregulation of UCP1, elongation of very long chain fatty acids like-3 (ELOVL3) and peroxisome proliferator-activated receptor γ 1-α (PGC1A), a major regulator of mitochondrial biogenesis, compared to non-FNDC5 differentiated cells. Conversely, leptin—a gene associated with white fat development—is down regulated in brown-adipose differentiated cells. Higher levels of expression of these brown adipocyte marker genes are consistent with a mature brown adipocyte fate. These findings demonstrate that brown adipose depots from newborns are a source of stem cells that have unique properties than stem cells found in adult brown adipose depots, subcutaneous adipose and visceral adipose depots, and have the ability to differentiate into multiple cell types.

Figure 4A:
FIG. 4(a) is a scanning electron microscopy (SEM) of brown adipose derived stem cells cultured on porous extracellular matrix scaffolds.
Figure 4B:
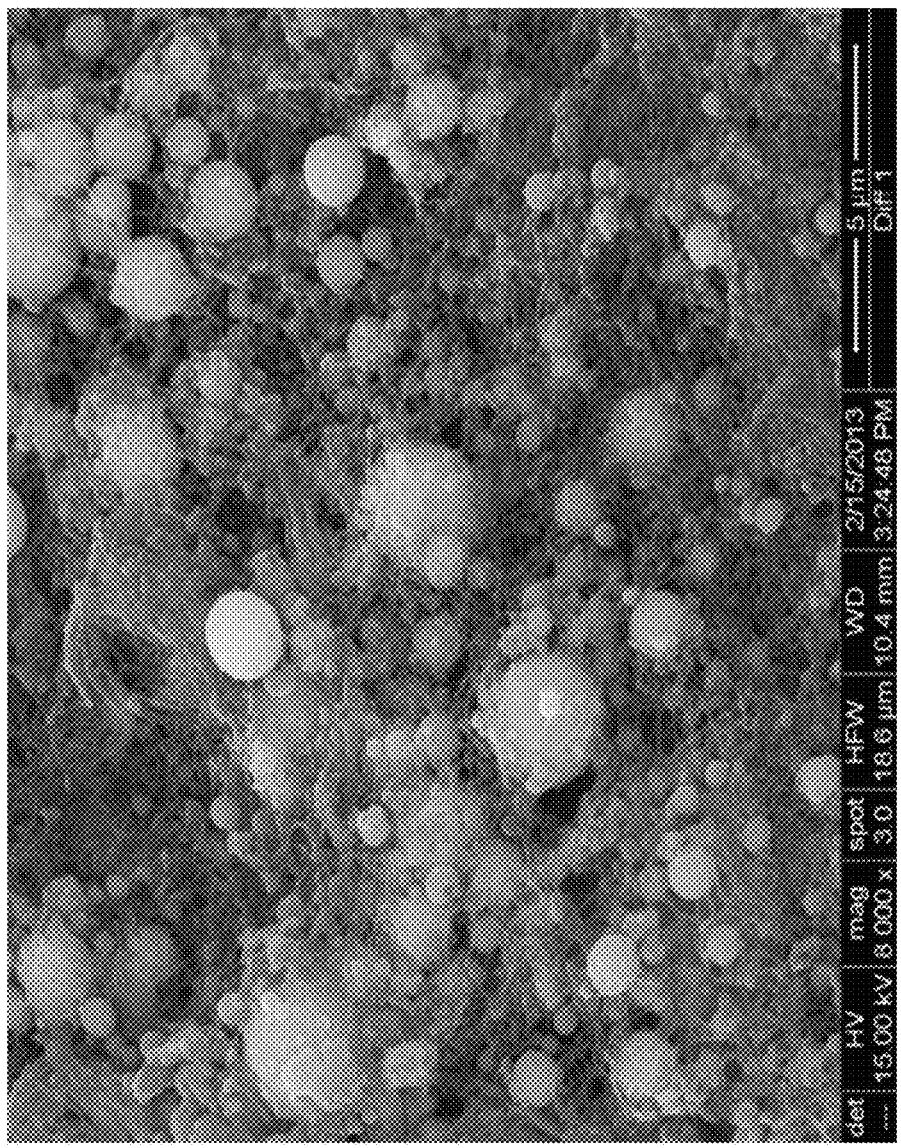
FIG. 4(b) is an SEM of directionally differentiated brown adipocytes on scaffolds.
Figure 5A:
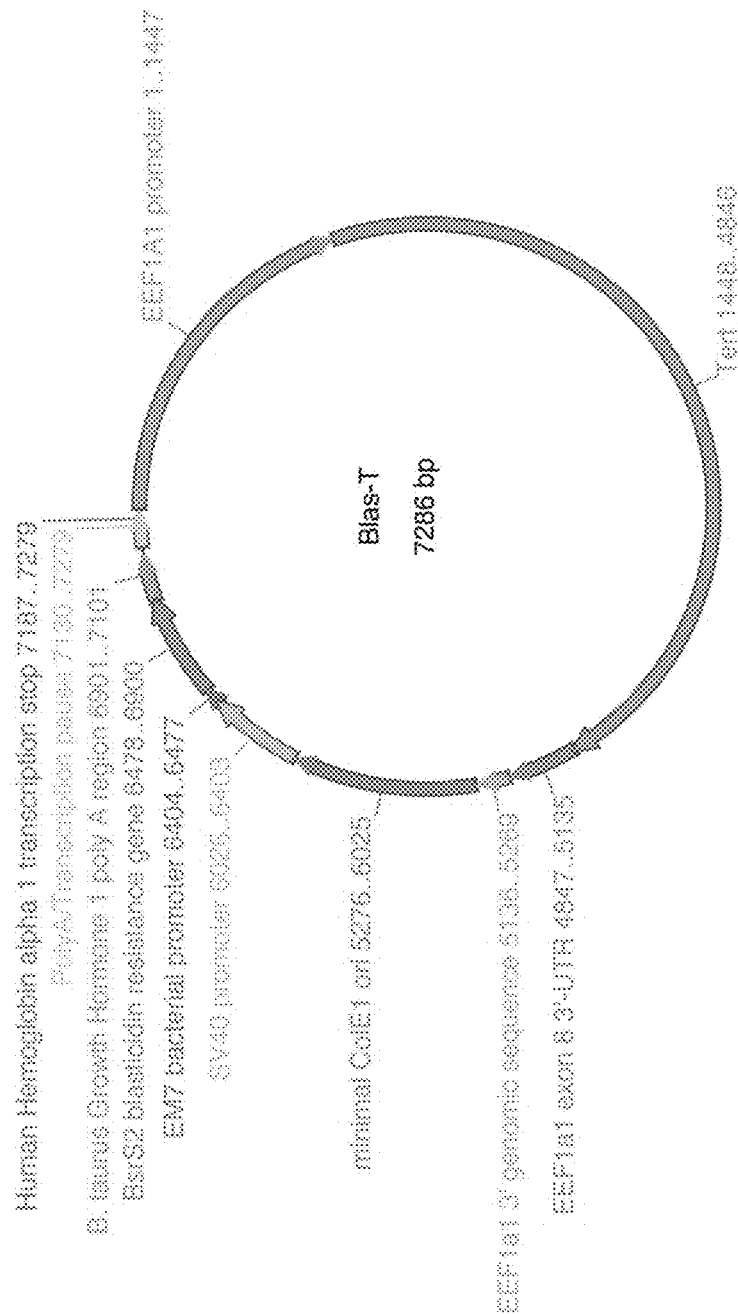
FIG. 5(a) is a map of a first transformation construct used to immortalize neonatal brown adipose derived stem cells.
Figure 5B:
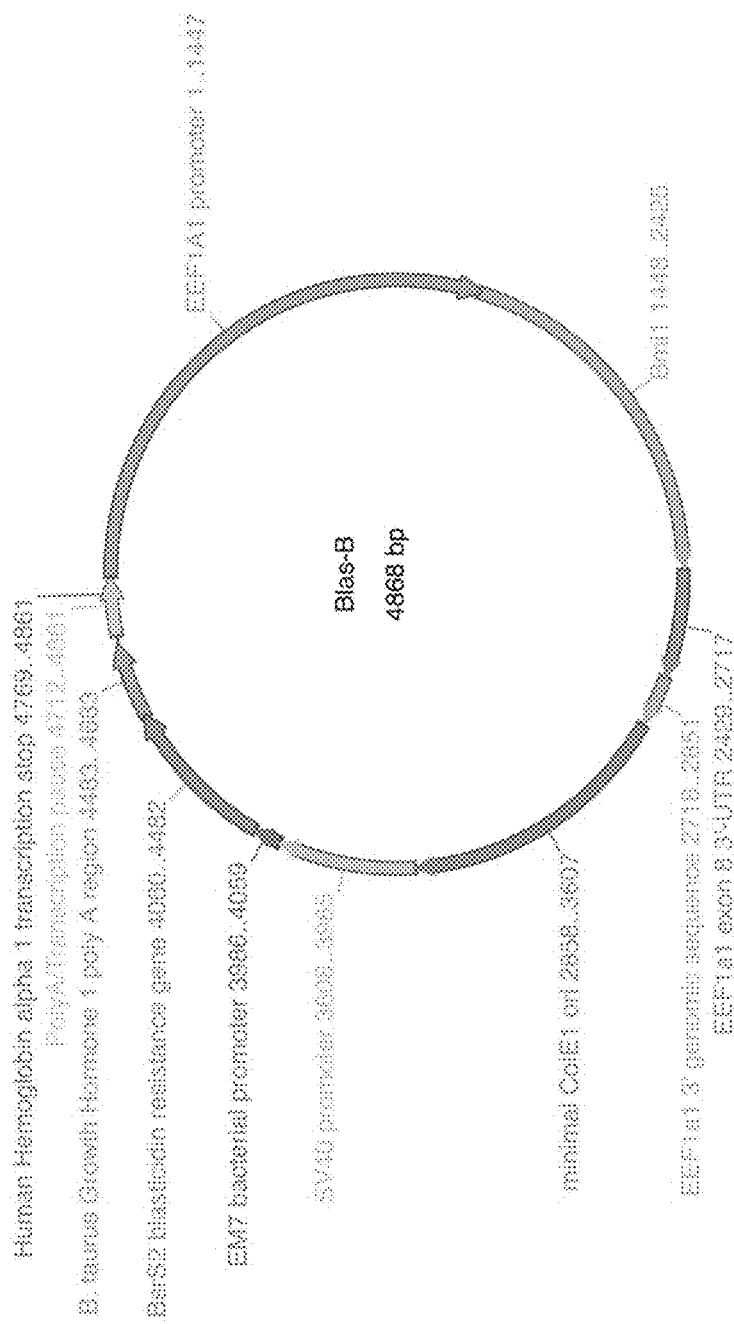
FIG. 5(b) is a map of a second transformation construct used to immortalize neonatal brown adipose derived stem cells.
Figure 5C:
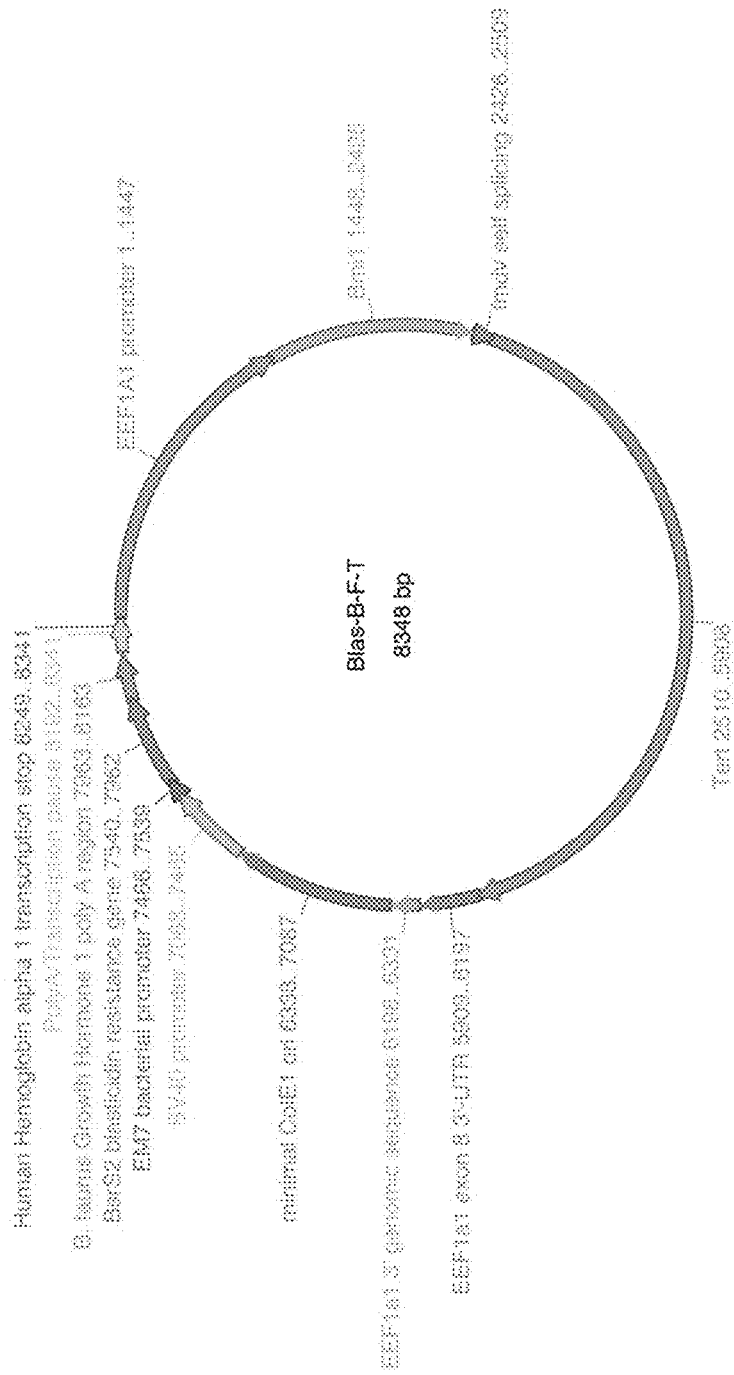
FIG. 5(c) is a map of a third transformation construct used to immortalize neonatal brown adipose derived stem cells.
Figure 5D:
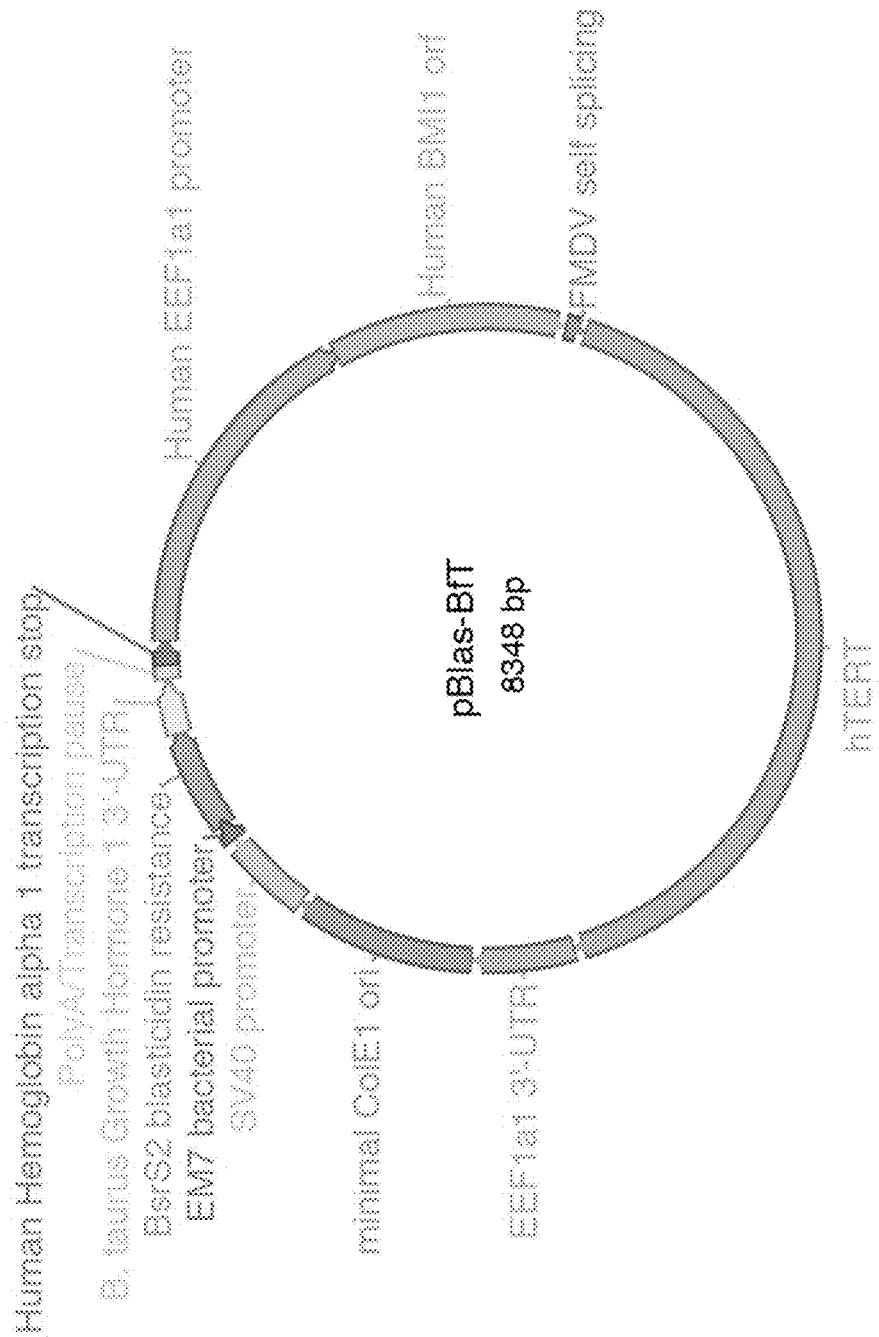
FIG. 5(d) is a map of a fourth transformation construct used to immortalize neonatal brown adipose derived stem cells.
Figure 5E:
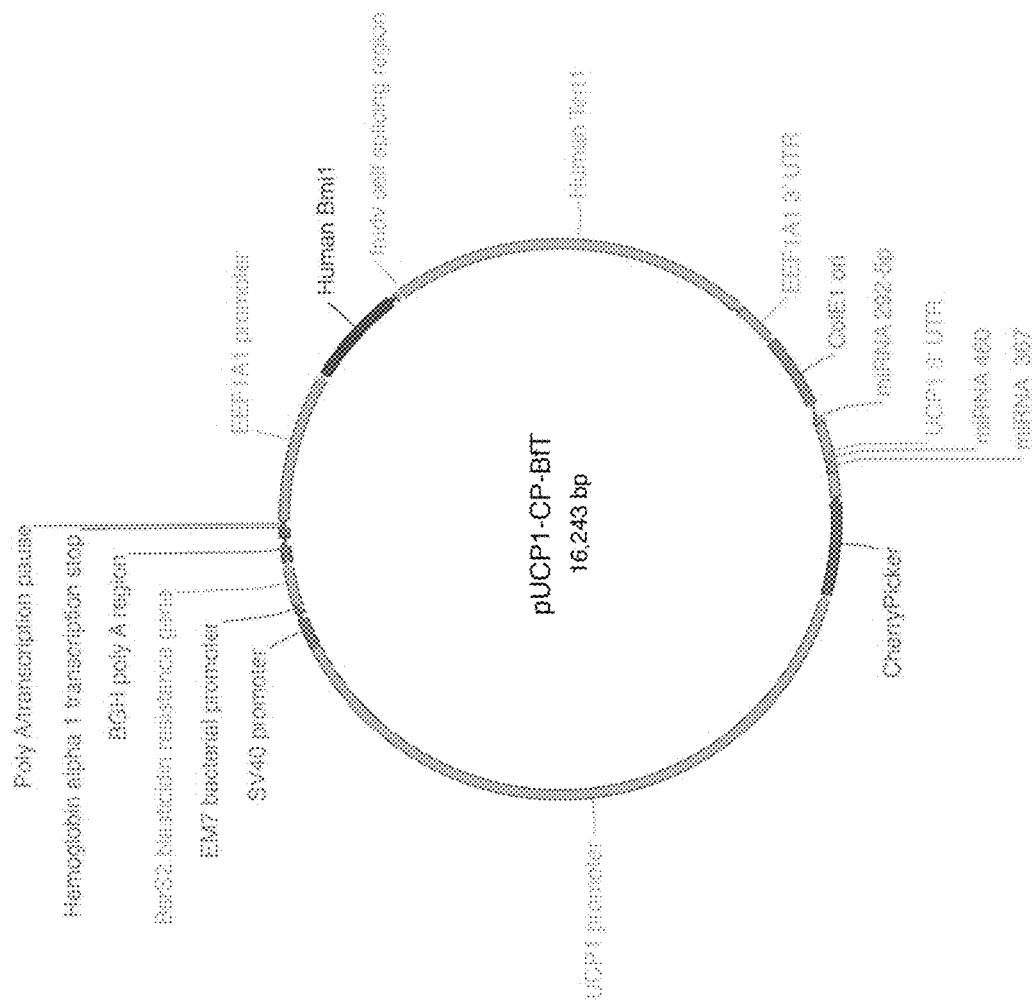
FIG. 5(e) is a map of a fifth transformation construct used to immortalize neonatal brown adipose derived stem cells.

BADSC in general can be grown on scaffolding as, as depicted in FIG. 4(a), and thereby made more easily handled for implantation and other experimentation.

In addition, various BADSC lines were immortalized by transfection. In one embodiment a BADSC150 line was used.

Five different plasmid constructs were created, as depicted in FIGS. 5(a)-5(e). These were a 7286 bp construct termed Blas-T, encoding an EEF1 promoter driving TERT expression, a 4868 bp construct termed Blas-B, encoding an EEF1 promoter driving BMI-1 expression; an 8348 bp construct termed Blas-B-F-T, encoding an EEF1 promoter driving both BMI1 and TERT expression, an 8348 bp construct termed pBlas-BIT encoding an EEF1a1 promoter driving both TERT and BsrS2, and a 16,243 bp construct termed pUCP1-CP-BfT encoding an EEF1A1 promoter driving expression of BMI1 and TERT and UCP1 promoter driving expression of a reporter gene cherry picker.

In one embodiment, the transfection used Lipofectamine LTX and PLUS reagent. In a second embodiment, the transfection used Fugene HD, Xfect Adult Stem Cell Transfection Reagent and Lipofectamine LTX with PLUS reagent according to manufacturers recommended protocol. Each reagent was tested for efficiency. Fugene HD was the least toxic to the cells and resulted in the highest transfection efficiency for BADSC150 primary cells transfected with construct Blas-BFT encoding EEF1 promoter driving expression of BMI1 and TERT (BMI1-TERT FMDV2-self processing polypeptide and TERT-BMI1 FMDV2-self processing polypeptide). Because the two orientations of the self processing polypeptides will function with differing efficiencies depending upon the cell line, both forms were tested in any given experiment.

In other embodiments, the BADSC150 line was transfected with the following combination of constructs listed below. The transfected cells with the blastocidin resistance gene were selected with a concentration of bug/ml. blastocidin. A stable immortalized brown adipose derived stem cell line was generated and tested for functional differentiation potential.

Under EEF1A1 control, all four resistance options were available:
pUNO-hpf Hygromycin;
pUNO-pur Puromycin;
pUNO-zeo Zeocin; and
pUNO-bla Blasticidin
The following single reporter systems were used:
mCherry alone;
NanoLuc (NL) alone; and
Secreted NanoLuc (sNL) alone.
The following combination Reporter systems were also used:
CP1-NL FMDV2-self processing polypeptide;
CP1-sNL FMDV2-self processing polypeptide;
NL-CP1 FMDV2-self processing polypeptide; and
sNL-CP1 FMDV2-self processing polypeptide.

In other experiments, the EEF1 promoter was also replaced with pro-brown (i.e. PRDM16, PGC-1α, C/EBPβ, Plac8 and UCP-1) and pro-white specific genes (i.e. PPARγ, C/EBPα, and AKT-1) used with different combinations of the reporter systems. All of these constructs contain EEF1 promoter driving expression of BMI1 and TERT.

Figure 6:
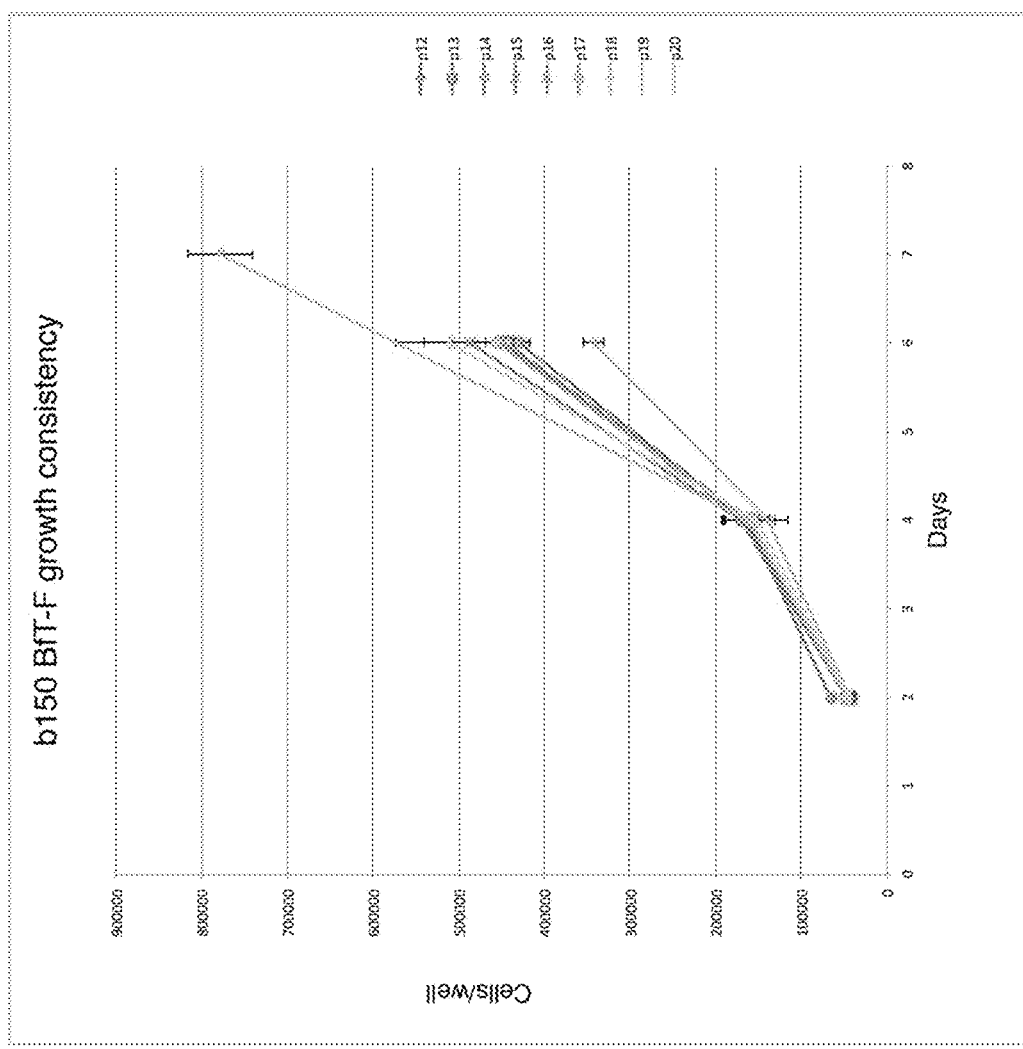
FIG. 6 is a graph of cell growth rate by passage.
Figure 7:
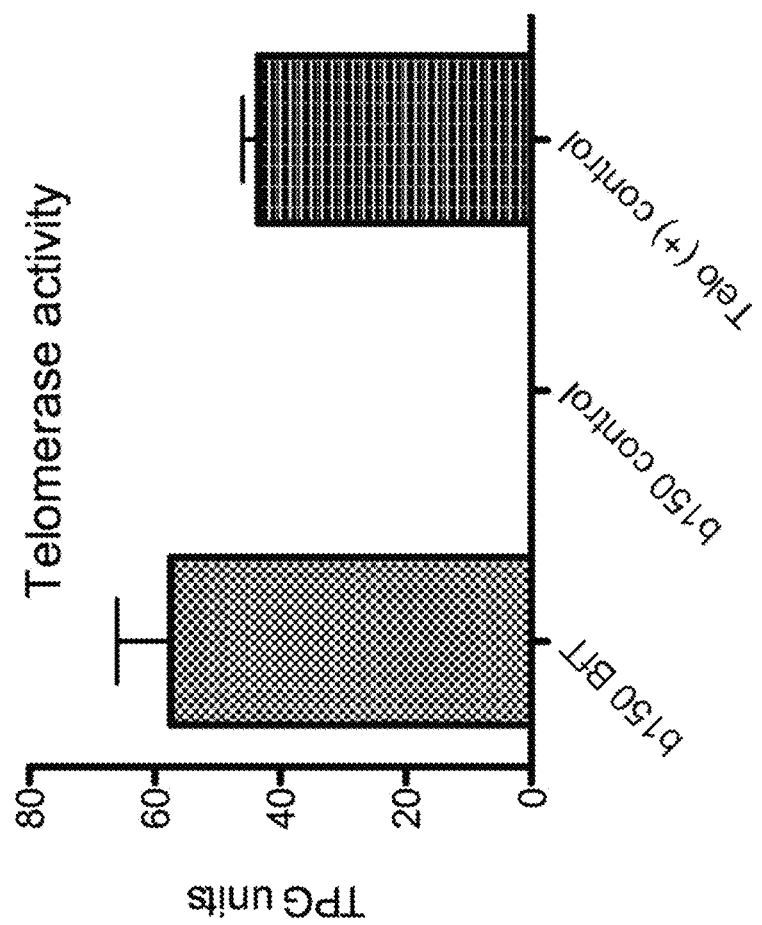
FIG. 7 is a graph of telomerase activity for transfected and control cells.

Once the BDSC150 cell line was transfected and selected, it was tested to determine the effects of extended passages. BADSC150 BMI1-TERT FMDV2-self processing polypeptide (FIG. 5($d$)) and TERT-BMI1 FMDV2-self processing polypeptide were passaged to p20 (FIG. 6). Cells expressed telomerase activity (FIG. 7) which was not present in the control (non-transfected BADSC150) and retained normal cell morphology (FIG. 8).

Figure 9:
FIG. 9 is a photomicrograph of BADSC having undergone white, brown adipogenesis.
Figure 10:
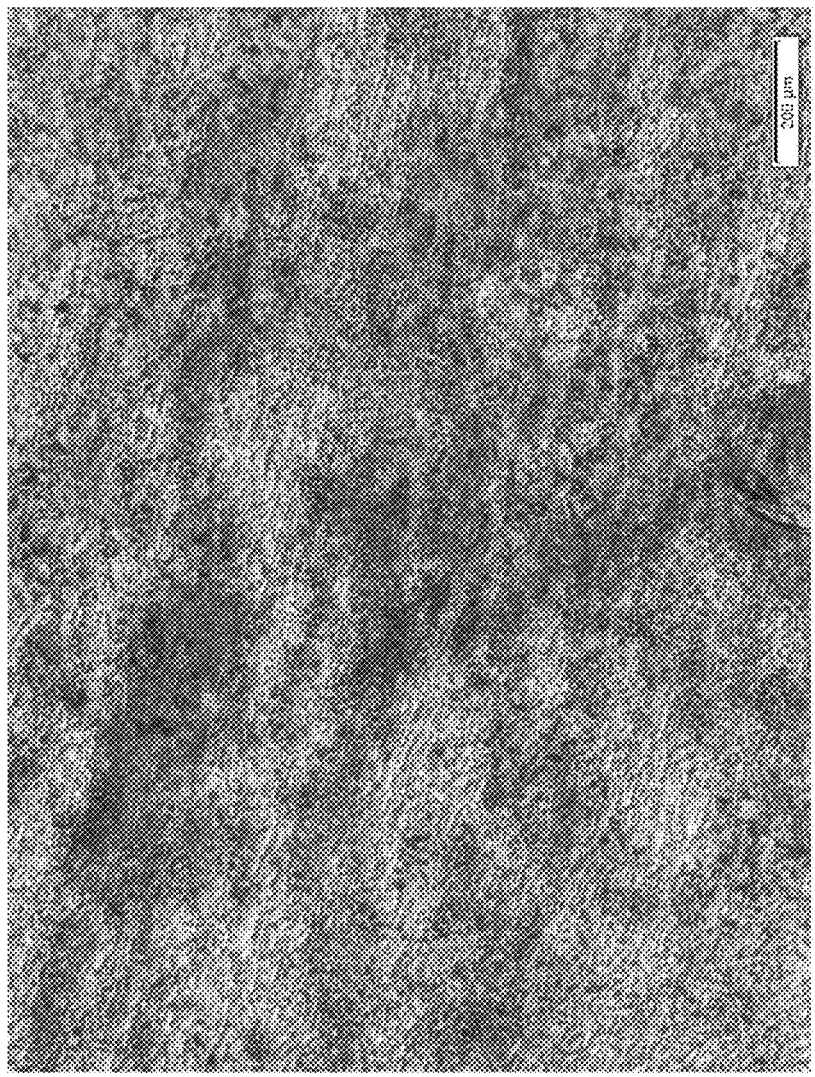
FIG. 10 is a photomicrograph of BADSC having undergone osteogenesis.
Figure 11:
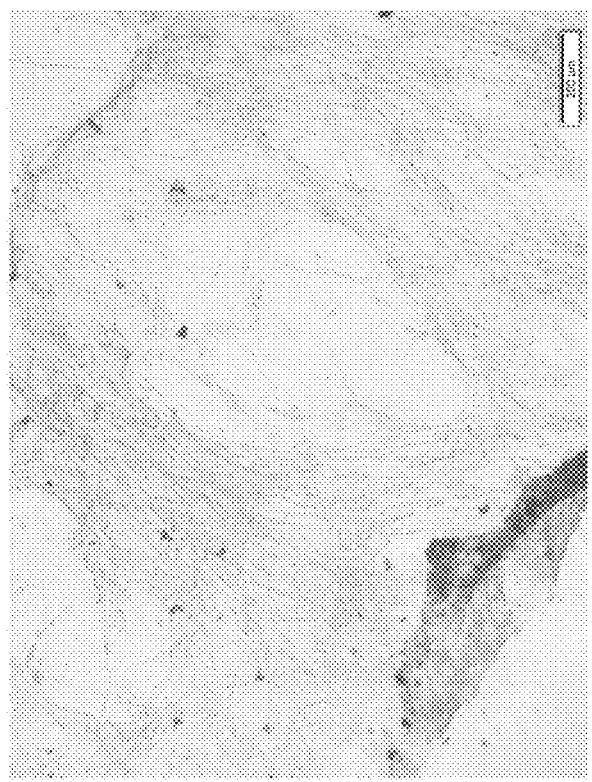
FIG. 11 is a photomicrograph of BADSC having undergone chondrogenesis.

Immortalized BADSC150 cells were also tested to determine their ability to functionally differentiate. Cells were induced to undergo white, brown adipogenesis (FIG. 9), osteogenesis (FIG. 10) and chondrogenesis (FIG. 11). This cell line with the different combinations of these constructs can be used to screen libraries of small molecules and brown adipose inducers (i.e. FNDC5, BMP7, retinoic acid).

In one combination, where the construct is UCP1-CherryPicker BM (FIG. 5($e$)), EEF1A1 is driving the expression of Bmi1 and Tert1. This construct is used to immortalize the cells. UCP1 is driving the expression of CherryPicker, chimeric membrane-anchored CherryPicker fluorescent protein, which can be monitored via fluorescence microscopy and be captured on magnetic beads using a specific antibody. In this embodiment, BADSC150 cells with this construct are immortal and CherryPicker is only activated when UCP1 is induced. The induction of UCP1 can be accomplished by exposing this cell population to either naturally occurring or synthetic small molecules that up-regulate brown adipose tissue specific genes.

In another embodiment, CherryPicker is replaced with secreted nanoluc (sNL). In this construct, sNL is synthesized only when the promoter is turned "ON". In one embodiment, the promoter is UCP1. Since sNL is secreted from the cell and into the cell culture media, one is able to assay the media for levels of sNL for a quantitative analysis of how efficacious the compound is for inducing UCP1 to turn "on" and in turn produce sNL. This system allows for high throughput screening of thousands of small molecules at different concentrations at one time.

Figures 12A, 12B:
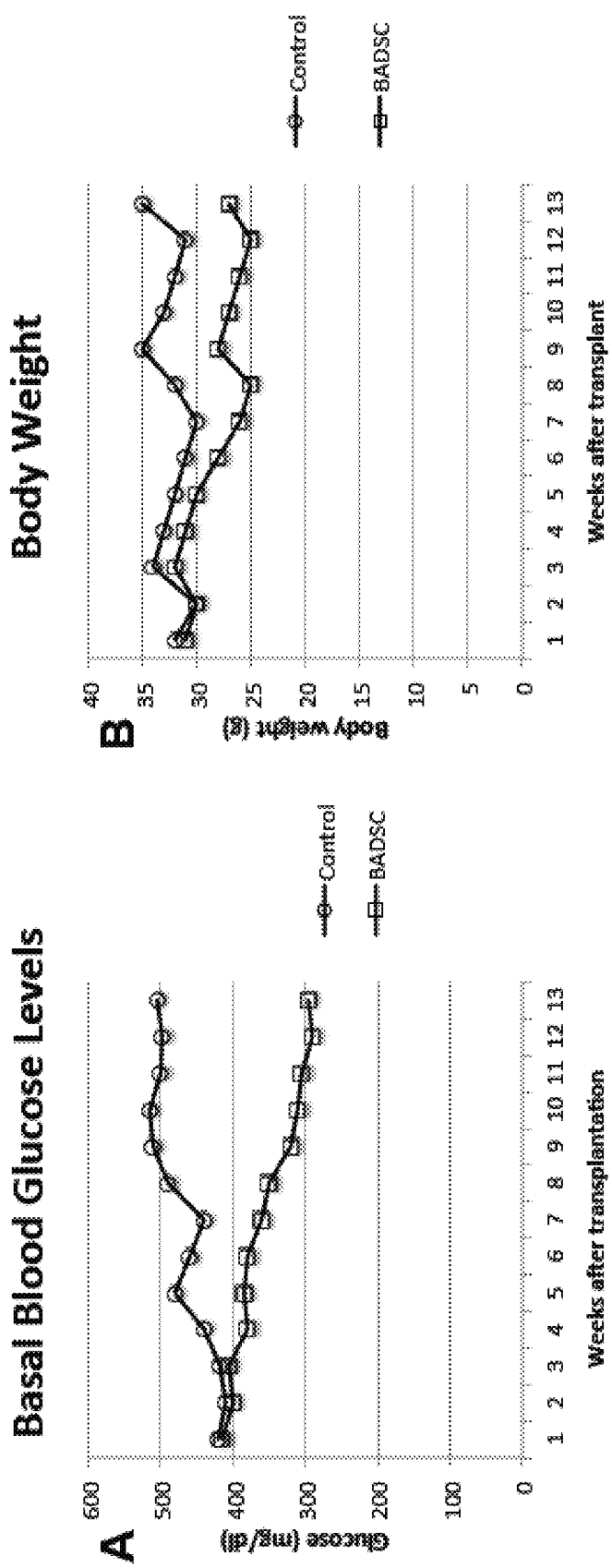
FIG. 12(a) is a graph of glucose levels of mice transplanted with BADSC/scaffolds and controls.
FIG. 12(b) is a graph of the weights of mice transplanted with BADSC/scaffolds and controls.

All combinations of constructs also have been transfected into white adipose stem cells for the purpose of identifying molecules that convert white fat into brown or increase metabolic activity. This cell line, in tandem with its reporter systems, permits for the effective study of the kinetics of brown fat biology; specifically, the mechanism underlying UCP1 up-regulation and increased metabolic activity. This human brown fat stem cell line is valuable due to the fact that the amino acid composition of mouse and human UCP1 is less than 80%, thereby rendering mouse brown fat cell lines inadequate for identifying compounds that activate brown fat specific genes In addition, a population of immortal implantable BADSC would provide a population of brown adipose tissue that can help regulate metabolism in humans. Referring to FIGS. 12($a$) and 12($b$), the two graphs show the effects of BADSC on scaffolds implanted in mice. FIG. 12($a$) shows that in the weeks after implantation, the basal blood glucose levels for control mice fed with a high calorie diet are significantly higher (about 66%) than mice fed with the same diet but implanted with BADSC. Similarly, in FIG. 12($b$) the body weight for the control mice is about 40% higher than the body weight of the mice with an implant. This indicates that BADSC may be useful in treating metabolic disorders such as diabetes and obesity.

The invention also provides a cell culture plate comprising human neonatal brown adipose derived cells. The plate can be, for example, a multiwell plate. One or more wells of the cell culture plate can be seeded with human neonatal brown adipose derived cells. The cells can be differentiated brown fat cells. The cells also can be immortalized. The cell culture plates are useful for screening drug compounds by contacting the cells with a candidate drug compound and observing the effect of the drug compound on the human neonatal brown adipose derived cell.

Figure 13:
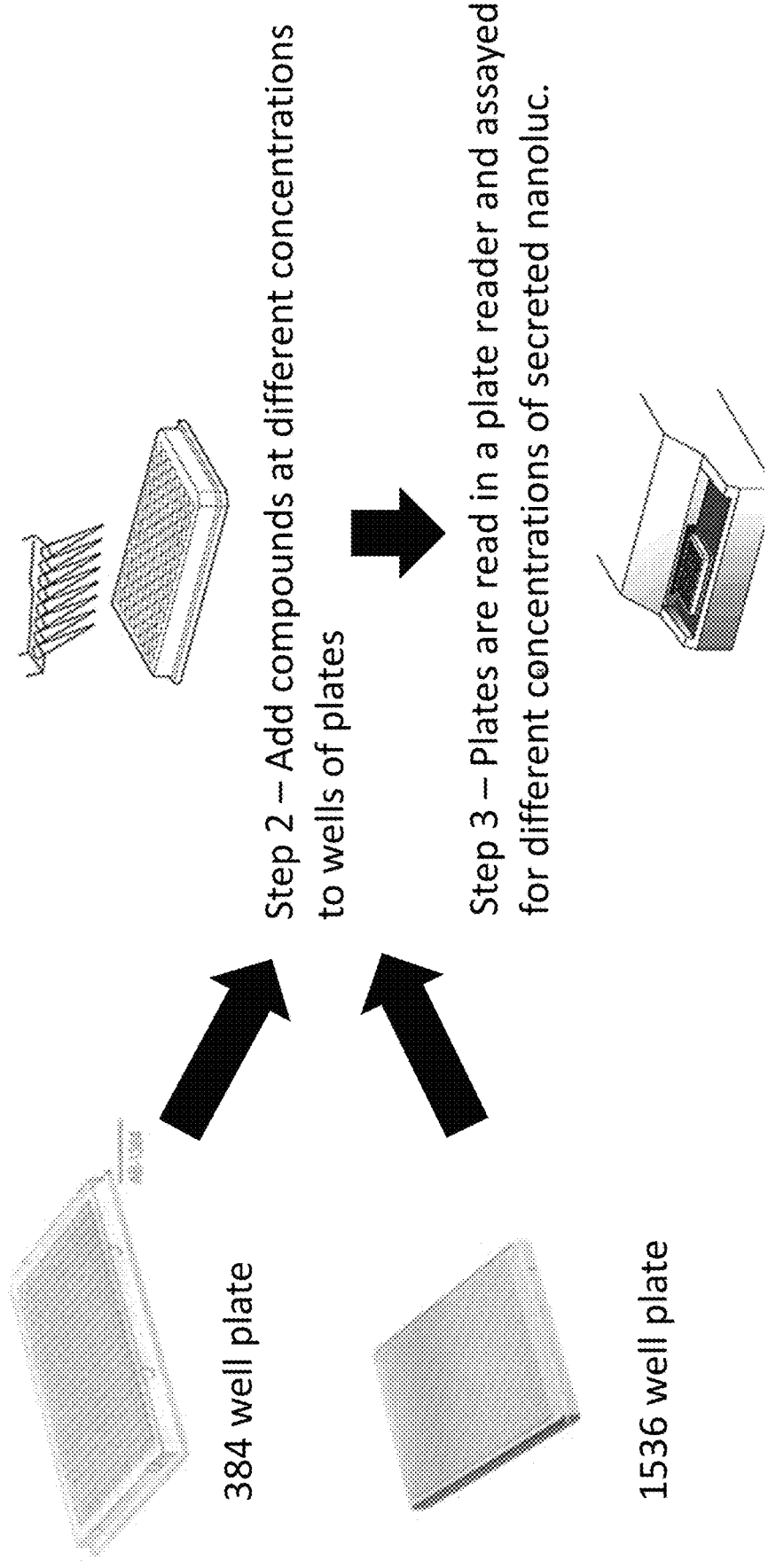
FIG. 13 is a depiction of the steps for high through-put analysis of compounds.

Referring to FIG. 13, such a screening method for various potential drugs begins by plating wells with either transfected BADSC cells (such as BADSC150FS.UCP1-sNL-BfT) or white adipose stem cells (such as WADSCFS.UCP1-sNL-Bft) (Step 1). Then the compounds of interest are added to the well (Step 2) and the wells are read in a plate reader and the media assayed for secreted nanoluc (Step 3), for example. The presence of nanoluc indicates that the drug has activated the stem cells.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

The invention claimed is:

1. An implantable construct comprising:
   a scaffold; and
   an isolated human neonatal brown adipose tissue stem cell cultured on the scaffold;
   wherein the isolated human neonatal brown adipose tissue stem cell is cultured in a culture medium comprising fibronectin type III domain-containing protein 5 (FNDC5) and differentiates into a human neonatal brown adipose tissue differentiated cell;
   wherein UCP-1, ELOVL3, and PGC1A gene expression is upregulated in the human neonatal brown adipose tissue differentiated cell.

2. The implantable construct of claim 1, wherein the scaffold comprises a porous extracellular matrix.

3. The implantable construct of claim 1, wherein the isolated human neonatal brown adipose tissue stem cell is derived from a one day old male neonate.

4. The implantable construct of claim 1, wherein the isolated human neonatal brown adipose tissue stem cell further expresses at least one of CREB1, DIO2, IRS1, MAPK14, NRF1, FOXC2, PPARD, PGC1-B, PRDM16, SRC, and WNT5A.

5. The implantable construct of claim 4, wherein the isolated human neonatal brown adipose tissue stem cell is derived from a one day old male neonate.

6. The implantable construct of claim 1, wherein the isolated human neonatal brown adipose tissue stem cell further expresses at least one of PPARGC1A and SIRT3.

7. The implantable construct of claim 6, wherein the isolated human neonatal brown adipose tissue stem cell is derived from a one day old male neonate.

8. The implantable construct of claim 1, wherein the isolated human neonatal brown adipose tissue stem cell is positive for the following cell surface markers: CD9, SSEA4, CD44, CD90, CD166, and CD73, and is negative for the following cell surface markers: CD14, CD34, CD45, and STRO-1.

9. The implantable construct of claim 8, wherein the isolated human neonatal brown adipose tissue stem cell is derived from a one day old male neonate.

10. The implantable construct of claim 1, wherein the human neonatal brown adipose tissue differentiated cell is a human brown adipocyte.

11. A method of treating a metabolic disorder in a patient, the method comprising: implanting the implantable construct of claim 1 in the patient.

12. A method of treating obesity in a patient, the method comprising:
    implanting the implantable construct of claim 1 in the patient.

13. A method of treating diabetes in a patient, the method comprising:
    implanting the implantable construct of claim 1 in the patient.

* * * * *